US005156654A

United States Patent [19]

Koch et al.

[11] Patent Number: 5,156,654

[45] Date of Patent: Oct. 20, 1992

[54] DETERGENT, DISPERSANT AND ANTI-RUST ADDITIVE FOR FUELS AND LUBRICATING OILS

[75] Inventors: Paolo Koch, Melegnano; Fulvio Giavazzi, San Giuliano Milanese, both of Italy

[73] Assignee: AGIP Petroli S.p.A., Rome, Italy

[21] Appl. No.: 515,845

[22] Filed: Apr. 10, 1990

[30] Foreign Application Priority Data

Apr. 21, 1989 [IT] Italy .............................. 20258 A/89

[51] Int. Cl.[5] .................... C10L 10/00; C07D 207/40; C07C 231/02

[52] U.S. Cl. ........................................ 44/331; 44/347; 548/520; 564/134; 564/138; 252/51.5 A

[58] Field of Search ........................ 548/520; 540/470; 564/134, 135, 136, 138; 44/339, 347; 252/51.5 A

[56] References Cited

U.S. PATENT DOCUMENTS

| | | | |
|---|---|---|---|
| 2,982,633 | 5/1961 | Andress | 44/71 |
| 3,373,111 | 3/1968 | LeSuer | 252/51.5 |
| 3,509,052 | 4/1970 | Murphy | 252/34.7 |
| 4,614,522 | 9/1986 | Buckley | 548/520 |

FOREIGN PATENT DOCUMENTS

| | | |
|---|---|---|
| 0299119 | 1/1989 | European Pat. Off. . |
| 2040696 | 2/1971 | Fed. Rep. of Germany . |

*Primary Examiner*—C. Warren Ivy
*Assistant Examiner*—Celia Chang
*Attorney, Agent, or Firm*—Oblon, Spivak, McClelland, Maier & Neustadt

[57] ABSTRACT

An additive for fuels and lubricating oils with detergent, dispersant and anti-rust properties is described, consisting essentially of the product of condensing a mixture of alkenylsuccinic acids or anhydrides of formula (I)

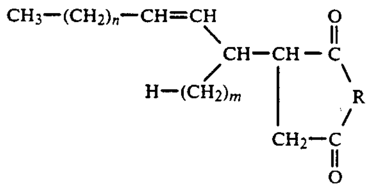

(I)

where m and n, mutually independently, represent 0 or a whole number between 1 and 10 and are such that their sum is 9 or 10, and >R is >O or (—OH, —OH), with triethylenetetramine of formula (II)

$$H_2N-(CH_2-CH_2-NH)_3-H \qquad (II).$$

6 Claims, No Drawings

DETERGENT, DISPERSANT AND ANTI-RUST ADDITIVE FOR FUELS AND LUBRICATING OILS

This invention relates to an additive for fuels and lubricating oils which possesses detergent, dispersant and anti-rust properties.

Said additive consists essentially of the product of condensing a mixture of alkenylsuccinic acids or anhydrides of formula (I)

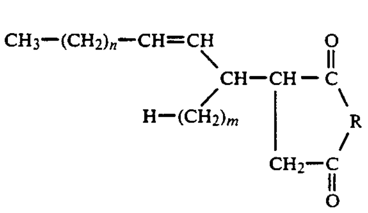

(I)

where: m and n, mutually independently, represent 0 or a whole number between 1 and 10 and are such that their sum is 9 or 10, and >R is >O or (—OH, —OH), with triethylenetetramine of formula (II)

$$H_2N—(CH_2—CH_2—NH)_3—H \quad (II)$$

The patent literature describes several classes of alkenylsuccinimide compounds and the use of these compounds as dispersant and detergent additives in fuels and lubricants is known. By way of example the following USA and European patents can be cited: U.S. Pat. Nos. 3,287,271, 3,172,892, 4,048,080, 3,216,936, 4,338,205, 3,401,118, 3,717,446, 3,131,150, 4,548,724, 3,799,877, EP-A-20,037 and EP-A-8,953. It remains however an objective of those working in this field to improve the performance of such formulations, for example by discovering compounds with greater activity or compounds which also exercise their activity under particular stress conditions or which exercise more than one property, or can be produced at lower cost, or allow more stable final products to be prepared, etc. It has now been found that the product obtained by condensing with triethylenetetramine a mixture of alkenylsuccinic acids or anhydrides of formula (I)

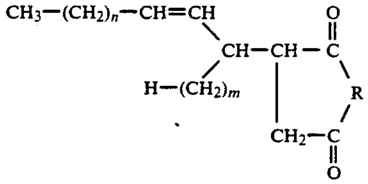

(I)

where: m and n, mutually independently, represent 0 or a whole number between 1 and 10 and are such that their sum is 9 or 10, and >R is >O or (—OH, —OH), possesses excellent detergent and dispersant characteristics together with considerable anti-rust activity, so that when this additive is added in suitable concentration to liquid fuel or lubricant compositions, it ensures perfect dispersion of any solid particles present in suspension, prevents the formation of deposits on the carburettor or injectors in the case for example of fuels, and at the same time completely prevents the formation of rust on the metal parts in contact with these fuels or lubricants.

It has been found in particular that excellent results are obtained if the mixture of alkenylsuccinic acids or anhydrides (I) is obtained by condensing maleic anhydride with a mixture of linear monoolefins of 13 and/or 14 carbon atoms having their double bond distributed statistically along the entire aliphatic chain. A mixture of this type is for example that obtained on catalytic dehydrogenation by conventional methods of the corresponding normal paraffins. In this case, by operating under suitable conditions monoolefin mixtures can be obtained in which the double bond is distributed statistically along the entire chain, even though preferentially inside it. To prepare the additive of the present invention the mixture of alkenylsuccinic acids or anhydrides (I) is reacted with triethylenetetramine (II) in a (I)/(II) molar ratio typically of between 2/1 and 1/1. The resultant product is a more or less complex mixture of mono- and bis-imides and amides, depending on the ratio of the two condensation partners. According to a preferred aspect of the present invention, if a (I)/(II) ratio of close to 2 is used, the predominant product is a mixture of bis-succinimides of general formula (III)

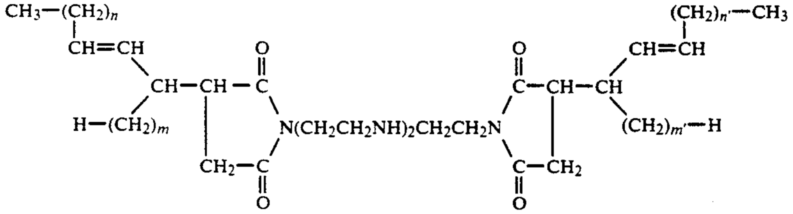

in which m and n have the meaning given heretofore, and m' and n' have the same definition as m and n although independent thereof. The preparation of alkenylsuccinic anhydrides (I) from maleic anhydride and a $C_{13}$ and/or $C_{14}$ monoolefin mixture can be described, for a particular value of n and m, by the following scheme:

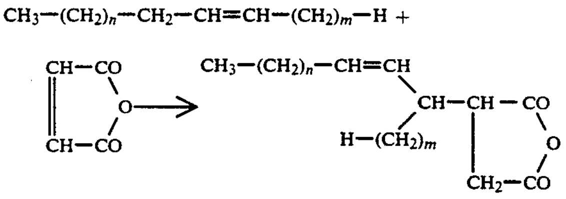

This reaction is generally conducted using an olefin/-maleic anhydride ratio of between 3/1 and 1/1 and preferably 1.5/1. The temperature of this reaction can vary from 140° to 270° C. but is preferably between 170° and 250° C., the yield being highest within this temperature range.

When the unreacted starting substances have been removed the mixture of alkenylsuccinic anhydrides (I)

obtained can be brought directly into contact with the triethylenetetramine (II) in a (I)/(II) molar ratio of between 2/1 and 1/1, and the condensation reaction can be conducted at a temperature typically of between 120° and 250° C. and preferably between 150° and 200° C. The condensation reaction is generally complete within a time period of between 1 and 6 hours, according to the chosen temperature. The water eliminated during the condensation reaction is removed from the reaction medium in order to displace the reaction equilibrium towards the products. For this purpose it can be convenient to conduct the reaction in the presence of an inert organic solvent which forms an easily distillable azeotrope with water such as toluene or xylene. The product obtained in this manner does not need particular treatment and can in fact be used as such as an additive in liquid fuels and lubricants. According to the present invention this product is added to liquid fuels and lubricants in a quantity sufficient to provide the desired dispersant and detergent activity and to inhibit rust formation on the metal parts in contact with the additive-containing fuels and lubricating oils.

The effective quantity is generally between 0.001 and 5% by weight and preferably between 0.01 and 3% by weight. The additive can be directly added as such to the fuel or lubricant, or the addition can be facilitated by using a concentrate containing from 25 to 95% by weight and preferably from 50 to 70% by weight of additive dissolved in a solvent-diluent which in a preferred aspect of the present invention can be the actual fuel or lubricating oil to which the additive is to be added, e.g. petrol, diesel oil, kerosene, mineral oils etc. Both the concentrate and the fuel or lubricant containing the additive of the present invention can contain other supplementary additives such as disemulsifying agents, antifoaming agents etc. in the case of fuels, and anti-wear agents, viscosity improvers etc. in the case of lubricants. Both the concentrate and the final fuel or lubricant can also contain other detergent, dispersant and/or anti-rust agents in quantities insufficient to provide the required effect.

The following non-limiting examples describe in greater detail the additive of the present invention and its preparation method, together with some of the tests used for evaluating the dispersant, detergent and anti-rust power of said additive.

EXAMPLE 1

Preparation of the new additive

An n-olefin mixture consisting of 58% tridecene and 40% tetradecene and having an average molecular weight of 187 (1069.79 g), maleic anhydride (373.76 g, 3.81 moles) and a small quantity of phenothiazine (1.5 g) acting as polymerization inhibitor during the synthesis are fed into a flask fitted with a mechanical stirrer, thermometer and reflux condenser. The mixture is heated while stirring under a nitrogen atmosphere to 180° C., condensing the maleic anhydride and olefin vapours. As the reaction proceeds the temperature is gradually raised to 220° C. and kept at this value for 13 hours. The excess olefin (413.65 g) and unreacted maleic anhydride (29.91 g) are recovered by distillation at 220° C., while progressively reducing the pressure in the reaction flask from atmospheric to about 10 mmHg (1330 Pa). The product obtained in this manner (1000 g, yield 92%) has a neutralization number of 200 mg KOH/g (titration by the ASTM D664 method), corresponding to an average molecular weight of 280.5. A part of the obtained product (500 g, 1.78 moles) and a silicone antifoaming agent (10 mg) are fed into a flask fitted with a mechanical stirrer, thermometer and condenser. The mixture is heated to 130° C. under stirring, then using a dropping funnel triethylenetetramine of 91.4% purity (138.6 g, 0.87 moles) is gradually added over a period of one hour. During the addition the temperature rises spontaneously to 180° C. On termination of the addition the reaction mixture is kept at 160° C. for two hours, removing the water which forms during the reaction by distillation. Water removal is completed by progressively reducing the pressure in the reaction flask from atmospheric to about 10 mmHg (1330 Pa) and maintaining the temperature at 150° C. for 30 minutes. The product obtained has a viscosity at 100° C. of 4.96 cSt, a freezing point of −9° C., a nitrogen content of 8% and a base titre, determined by the ASTM D2896 method, of 157 mg KOH/g.

EXAMPLE 2

Evaluation of anti-rust power

(a) In fuels

A steel pin is rotated for 24 hours in a vessel containing a mixture of 300 g of fuel (diesel oil or petrol) and 30 g of distilled water maintained at 60° C. (ASTM D665/A test). The rust formed on the pin is then evaluated. In the case of non-additived fuel the pin is completely covered with rust after 24 hours. In contrast, if 50 ppm of the compound of Example 1 are added to the fuel, the pin is covered with only a few points of rust, whereas if 100 ppm of the additive of Example 1 are added the pin is completely free of rust.

(b) In automotive lubricants

In the case of automotive lubrication oils the anti-rust power was evaluated both by the aforesaid ASTM D665/A test and by a Sequence IID engine test using a V-8 Oldsmobile engine bench-operated for 32 hours in accordance with the ASTM STP 315 procedure using as lubricant a control lubricant not containing the additive of Example 1 and, in a parallel test, the same lubricant but containing 0.15% of the product of Example 1. The control lubricant formulation was based on mineral oil containing 1.3% of zinc dithiophosphate, 4.5% of an ashless dispersant and 1.5% of a detergent consisting of a superbasic calcium sulphonate (12% of calcium by weight) having a viscosity at 100° C. of 12.5 cSt. The result of the engine test is considered positive if the evaluation of the engine components at the end of the test, expressed as a score out of ten, exceeds 8.5. In the ASTM D665/A test the control lubricant not containing the anti-rust additive gave a pin 50% covered with rust, whereas in the sequence IID engine test it gave an average rust score of 7.5. In contrast the lubricant containing 0.15% of the additive of Example 1 gave a pin completely free of rust in the ASTM D665/A test and an average score of 8.7 in the engine test.

EXAMPLE 3

Evaluation of detergent power

(a) In diesel oil

The detergent power was evaluated by an engine injector detergency test using a commercial diesel oil without detergents as the control and the same diesel oil with 100 ppm of the product of Example 1 added. Specifically, a boosted Peugeot XD2S diesel engine fitted with DN OSD 252 Bosch injectors was used, bench-operated for 20 hours. Before and after the test the injector throughput is measured at different needle lifts (0.1 and 0.3 mm), these measurements being used to calculate the percentage throughput reduction due to deposit formation. In the case of the commercial diesel oil without additive, the average throughput reduction is 76.5%. With the diesel oil comprising 100 ppm of the product of Example 1, this average reduction is 60.5%, corresponding therefore to a reduction of 21% in the injector deposits compared with the diesel oil without additive.

(b) In petrol

The detergent power was evaluated by an engine detergency test on the carburettor using a commercial petrol as control and the same petrol with 100 ppm of the product of Example 1 added. Specifically, a Renault R5 petrol engine was used, bench-operated in accordance with the CEC F-03-T-81. The evaluation is carried out using a conventional merit scale from 1 to 10, where 10 corresponds to the carburettor completely clean.

The petrol without additive merited a score of 3.7 in this engine test, whereas the petrol with 100 ppm of the product of Example 1 added merited a score of 8.8.

EXAMPLE 4

Evaluation of dispersant power

Diesel oil normally contains variable quantities of carbon particles in suspension. In diesel engines, where a filter system is incorporated into the fuel feed circuit, the accumulation of these deposits causes a progressive fall in fuel throughput until the filter is completely clogged. The solubilizing/dispersing effect exercised on these deposits by the product of Example 1 was evaluated using a filter system simulating that used in diesel engines and measuring the time required to filter, under equal conditions, equal volumes of commercial diesel oil containing 100 ppm of the product of Example 1 and of the same diesel oil without additive. In the first case the filtration time was 12 minutes and in the second case 26 minutes.

We claim:

1. A method of providing a fuel or lubricating oil with detergent, dispersant and anti-rust properties, comprising:

adding to said fuel or lubricating oil an effective amount of a succinimide compound prepared by condensing a mixture of alkenylsuccinic acids or anhydrides of formula (I)

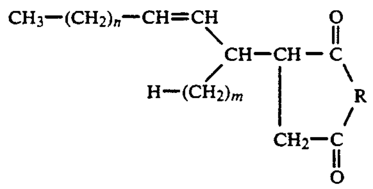

(I)

wherein m and n, mutually independently, represent 0 or a number between 1 and 10 and are such that the sum is 9 or 10, and R is O or (—OH,—OH), with triethylenetetramine of formula (II)

$$H_2N-(CH_2-CH_2-NH)_3-H \quad (II)$$

at a temperature of 120° to 250° C. and at a mole ratio of acid or anhydride to amine of 2/1 to 1/1.

2. The method claimed in claim 1, wherein from 0.001 to 5% by weight of the additive is added to said fuel or lubricating oil.

3. The method claimed in claim 2, wherein the amount of said additive ranges from 0.01 to 3% by weight.

4. The method claimed in claim 1, wherein said ratio is approximately 2.

5. The method claimed in claim 1, wherein the alkenyl group of the succinic acid or anhydride originates from a mixture of linear monoolefins having 13 and/or 14 carbon atoms in their chain, in which the double bond is distributed statistically along the chain.

6. The method as claimed in claim 5, wherein the mixture of linear monoolefins having 13 and/or 14 carbon atoms in their chain, in which the double bond is distributed statistically along the chain, originates from the catalytic dehydrogenation of the corresponding linear paraffins.

* * * * *